United States Patent [19]

Hardwick

[11] 4,192,301
[45] Mar. 11, 1980

[54] RE-BREATHING APPARATUS

[76] Inventor: Charles W. Hardwick, 712 W. 25th St., Sanford, Fla. 32771

[21] Appl. No.: 957,872

[22] Filed: Nov. 6, 1978

[51] Int. Cl.$^2$ .............................................. A61M 16/00
[52] U.S. Cl. ............................ 128/205.17; 128/205.24
[58] Field of Search ................. 128/202, 145.7, 145.8, 128/205, 188, 197, 209, 210, 727, 728; 272/99 R; 46/87, 88

[56] References Cited

U.S. PATENT DOCUMENTS

| 743,294 | 11/1903 | Knowles | 128/202 |
|---|---|---|---|
| 2,007,330 | 7/1935 | Hicks | 128/202 X |
| 3,513,843 | 5/1970 | Exler | 128/202 |
| 3,859,997 | 1/1975 | Douma et al. | 128/202 |
| 3,949,984 | 4/1976 | Navara | 272/99 R |
| 4,037,595 | 7/1977 | Elam | 128/145.7 |
| 4,086,923 | 5/1978 | Henkin | 128/202 X |

*Primary Examiner*—Henry J. Recla
*Attorney, Agent, or Firm*—Duckworth, Hobby, Allen & Pettis

[57] ABSTRACT

A disposable re-breathing apparatus for use with hyperventilating patients has a disposable, flexible polymer bag which attaches to a nose/mouth mask and an air control valve located between the mask and the disposable bag which adjusts the ratio of re-breathed air to fresh air through a fresh air inlet. The fresh air inlet has a check valve preventing exhaling air therethrough and a pressure relief valve may be provided to release re-breathed air when the polymer bag becomes filled.

10 Claims, 5 Drawing Figures

RE-BREATHING APPARATUS

BACKGROUND OF THE INVENTION

The present invention relates to a disposable re-breathing device for hyperventilation patients, and especially to one that provides greater control of the amount of re-breathed air.

DESCRIPTION OF THE PRIOR ART

Hyperventilation or over-breathing is brought on by anxiety, fear, and the like, which may result from accidents, emotional disorders, or trauma, and results in an excessive loss of carbon dioxide from the bloodstream. This, in turn, causes numbness, tingling and a feeling of shortness of breath, which is frequently treated in Emergency Rooms and by personnel in emergency type vehicles. Treatment has typically been by having the patient rebreath exhaled air that is rich in carbon dioxide and typically, a common kraft paper bag is used for the patient to breath into to restore the normal acid/base balance in the blood. However, some patients are insulted or offended by the use of a common, non-professional appearing paper bag, and professional devices that are used are frequently expensive and require resterilization for the safety of the patient.

A typical re-breathing bag can be seen in U.S. Pat. No. 2,304,033 for a sanitary re-breathing bag using a paper bag, but modified with tubes attached to the bag. A more elaborate rebreathing device may be seen in U.S. Pat. No. 2,007,330 for a self-administering carbon dioxide apparatus having an inflatable nose/mouth mask connected by a tube to an inflatable rubber bag. U.S. Pat. No. 3,513,843 has a respiratory device for rebreathing carbon dioxide of a more elaborate type using a nose/mouth mask connected to a collapsible sack mounted to a flange and having a fixed bottom having a valve therein and a stem spacing the flanged portion with the bottom portion and also having a breather valve. U.S. Pat. No. 3,455,294 teaches a respiratory device for increasing the depth and volume of respiration of the patient.

In contrast, the present invention provides an inexpensive nose/mouth mask connected to a simple proportioning valve which can vary the proportion of air re-breathed with the proportion of fresh air inhaled by the patient by the turning of a single control knob. The present re-breathing device advantageously allows the use of commonly available small plastic bags and a plastic mask and valve, which are sufficiently inexpensive to allow each patient to have a new disposable unit.

SUMMARY OF THE INVENTION

A re-breathing apparatus is provided with a nose/mouth mask for a patient to breath into and is connected through a pipe to a disposable, flexible re-breathing bag made of a polymer material which is operatively coupled to the mask. An air control valve is connected between the mask and the bag to vary the ratio of air between air being re-breathed from the bag and fresh air from a fresh air inlet connecting the valve to the open atmosphere. The fresh air inlet has a check valve therein to prevent the patient's exhaled air from being exhaled into the open atmosphere. A pressure relief valve may also be provided, if desired, to prevent the bursting of the plastic bag from excessive pressure.

BRIEF DESCRIPTION OF THE DRAWINGS

Other objects, features and advantages of the present invention will be apparent from the written description and the drawings, in which.

DESCRIPTION OF THE PREFERRED EMBODIMENT

Figure 1:
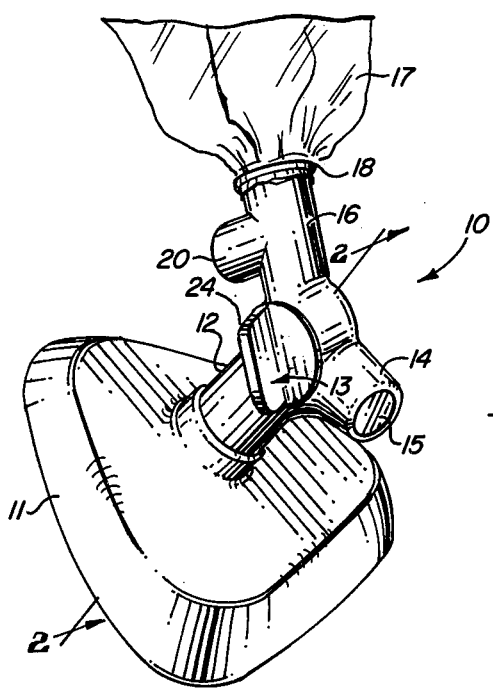
FIG. 1 is a perspective view of a re-breathing device in accordance with the present invention.

Referring to the drawings, and especially to FIG. 1, a re-breathing device 10 is provided with a nose/mouth mask 11 which is connected by a tube 12 to a control valve 13. The control valve is also connected to an air inlet tube 14 having a flap type check valve 15 and through a tube 16 to a flexible polymer bag 17, such as the simple, inexpensive polymer bags commonly available in supermarkets. The bag 17 may be attached with a fastener means 18, which can be a flexible, resilient fastener, such as a rubber band, if desired. The tube 16 has a tube opening 20 opening to the atmosphere with a pressure relief valve located therein.

Figure 2:
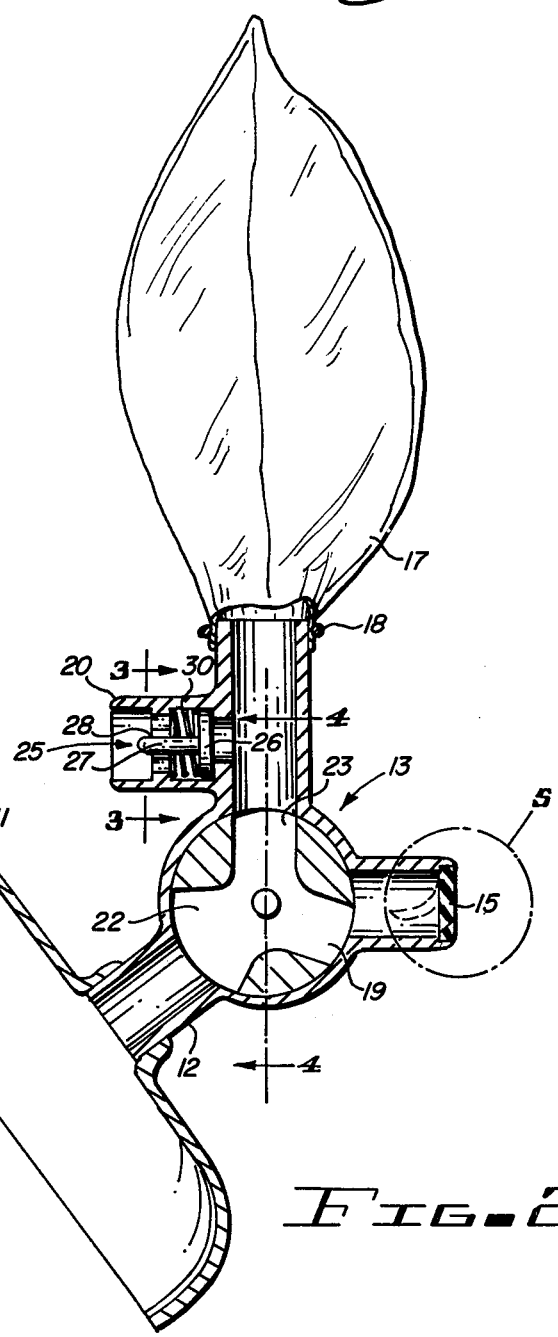
FIG. 2 is a sectional view taken on the line 2—2 of FIG. 1.

The operation of the system can be more clearly understood in connection with FIG. 2, in which it can be seen that the patient breathes into the nose/face mask 11 thereby inhaling and exhaling air through the tube 12 into the valve 13 which is a "Y" valve having a rotating valve element 21 having a wide passageway 22 opening onto the tube 12, a smaller passageway 19 opening onto the air inlet tube 14 and a similar passageway 23 opening onto the tube 16.

Rotation of the handle 24, as seen in FIG. 1, rotates the valve element 21 to vary alignments of the passageways 22 with the opening 12, and 19 with the opening 14, and 23 with the tube 16 to vary the proportion of air inhaled through the tube 14 and into the atmosphere. Thus, all of the air exhaled by the patient is directed into the bag 17 until the bag 17 is completely filled at which time a pressure relief valve 25 will direct air through the opening 20 to the atmosphere. The pressure relief valve 25 includes a valve element 26 attached to a sliding guide 27 sliding in a support element 28 and spring loaded by a spring 30, which can apply predetermined pressure to allow the valve 25 only to open when a predetermined pressure differential exists on both sides of the piston 26. Thus, the valve 25 controls the air exhaled into the atmosphere when the polymer bag 17 is completely filled, while the air inlet 14 and check valve 15 control the intake of fresh air by the varying of the control valve 13 by the rotation of handle 24.

Figure 3:
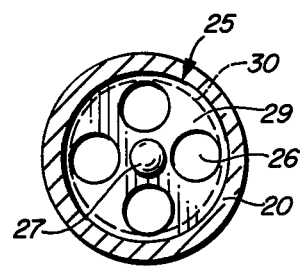
FIG. 3 is a sectional view taken on the line 3—3 of FIG. 2.

FIG. 3 more clearly illustrates the tube 20 and frame member 29 of the pressure relief valve 25 having the guide rod 27 and the relief spring 30 pushing against the piston 26.

Figure 4:
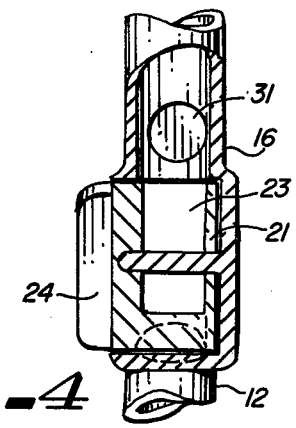
FIG. 4 is a sectional view taken on the line 4—4 of FIG. 2.

FIG. 4 shows a sectional view of the valve 13 having the handle 24 connected to the valve element 21 with an opening 23 connected to the tube 16 adjacent an opening 31 into the tube 20. The tube 12 can also be seen in this view.

Figure 5:
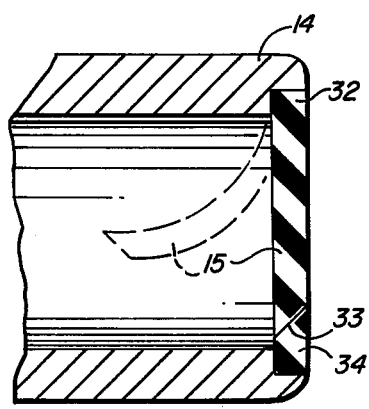
FIG. 5 is a sectional view taken on the circle 5 of FIG. 2.

In FIG. 5, the tube 14 can be seen having a flapper valve element 15 acting as a check valve and being fastened at 32 to the tube 14 and being angled at 33 for engaging a valve seat 34 on the other side thereof so that the flapper element 15 can be pulled into the tube 14 by a pressure differential by the inhaling of air by a patient into the mask 11, but exhaling by the patient will direct the valve element 15 against the seat 34 and prevent exhaled air from passing out the tube 14.

It should be clear at this point that a re-breathing apparatus has been provided which allows a more professional appearing device for use with patients, but which allows for the rapid change of inexpensive polymer bags 17 for sanitary purposes and easy control of the ratio of re-breathed to fresh air by a single control handle 24. This system, however, is not to be considered as limited to the particular forms shown herein, which are to be considered illustrative rather than restrictive.

I claim:

1. A disposable re-breathing apparatus comprising in combination:
   disposable mask for a patient to breath into;
   disposable, flexible re-breathing bag operatively coupled to said mask;
   air control valve means connected between said mask and said bag and providing a bi-directional flow path therebetween and having a fresh air inlet connecting said air control valve means to the open atmosphere;
   a check valve operatively attached to said fresh air inlet to prevent the exhaling of air from said fresh air inlet; and
   said air control valve means having valving means for varying the ratio of air breathed by a patient from said mask between re-breathed air from said bag and fresh air from said fresh air inlet, thereby providing a greater control of re-breathing by patients.

2. The re-breathing apparatus in accordance with claim 1, in which a relief valve is mounted between said mask and said disposable flexible re-breathing bag to allow the escape of exhaled air by a patient when said re-breathing bag is filled.

3. A re-breathing apparatus in accordance with claim 2, in which said disposable, flexible re-breathing bag is a thin polymer bag.

4. The re-breathing apparatus in accordance with claim 3, in which a resilient band removably attaches said disposable, flexible re-breathing bag to said air control valve, thereby operatively connecting the bag to said mask.

5. A re-breathing apparatus in accordance with claim 4, in which said air control valve means includes a valve housing having a first port connected to said bag, a second port connected to said air inlet, and a third port connected to said mask, and said valving means includes a rotating valve element having an external handle rotatably mounted in said housing to adjust the ratio of fresh air to re-breathed air.

6. A re-breathing apparatus in accordance with claim 5, in which said rotatable valve element has Y-shaped passageways therethrough having a first leg substantially aligned with said first port, a second leg substantially aligned with said second port and a third leg substantially aligned with said third port and is rotatable to vary said passageway openings defined by said ports between said mask and said fresh air inlet opening and between said mask and said flexible re-breathing bag.

7. The re-breathing apparatus in accordance with claim 6, in which said rotatable valve element third leg has a larger passageway than the other legs and wherein the angle between the first and second legs is ports larger than the angle between the first and second ports whereby said air inlet can be completely closed and gas flow is permitted between said mask and bag.

8. A re-breathing apparatus in accordance with claim 7, in which said check valve is a flexible flapper type check valve attached to an opening tube opening into said control valve.

9. The re-breathing apparatus in accordance with claim 8, in which said flapper check valve includes a valve seat for seating said flapper element when air is exhaled into said air inlet tube, but allowing said flapper element to swing open to allow air into said control valve and mask.

10. The re-breathing apparatus in accordance with claim 2, in which said relief valve includes a piston mounted to a guide rod and spring loaded against a valve seat to allow air to escape during a patient's exhaling only when a predetermined pressure is applied against said piston.

* * * * *